Figure 1:
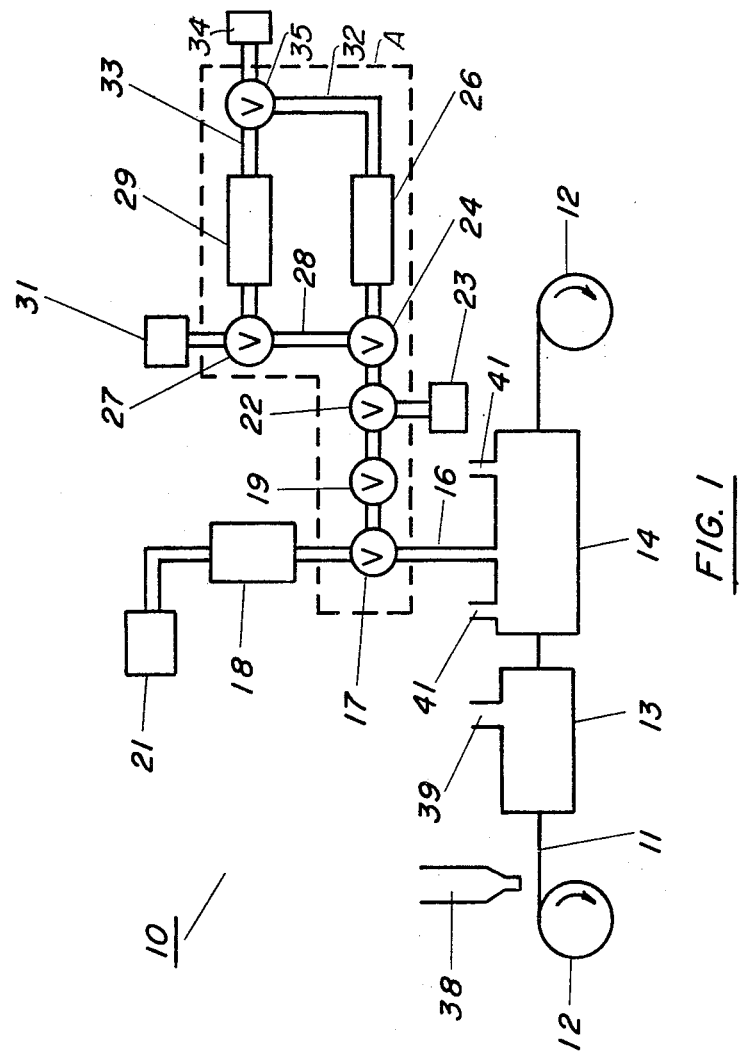

United States Patent [19]
Dugger

[11] 3,954,408
[45] May 4, 1976

[54] APPARATUS AND PROCESS FOR CHROMATOGRAPHIC PRODUCT DETECTION

[75] Inventor: Harry A. Dugger, Morristown, N.J.
[73] Assignee: Sandoz, Inc., E. Hanover, N.J.
[22] Filed: Nov. 29, 1974
[21] Appl. No.: 528,343

[52] U.S. Cl. .................. 23/230 PC; 23/253 PC; 23/232 C
[51] Int. Cl.² .................. G01N 31/08; G01N 31/10; G01N 31/12
[58] Field of Search ...... 23/230 PC, 253 PC, 232 C, 23/230 M, 232 E, 254 E, 255 E, 230 R; 73/23.1, 23

[56] References Cited
UNITED STATES PATENTS

| | | | |
|---|---|---|---|
| 2,634,360 | 4/1953 | Kusa | 23/253 PC X |
| 3,128,619 | 4/1964 | Lieberman | 23/230 PC UX |
| 3,292,420 | 12/1966 | Scott | 73/23.1 |
| 3,692,492 | 9/1972 | Poli, Jr. et al. | 23/232 E X |

Primary Examiner—Robert M. Reese
Attorney, Agent, or Firm—Gerald D. Sharkin; Robert S. Honor; Walter F. Jewell

[57] ABSTRACT

Apparatus and process for detecting the products of either liquid or gas chromatographic analysis, which products may be either radioactively tagged or not tagged. In one aspect, it provides a moving wire apparatus for conveying a liquid chromatographic sample through a combustion furnace, where the combustion products are conveyed to a catalytic system. Non-radioactive samples are routed through a nickel catalytic converter; and thence, to a flame ionisation detector. Radioactive samples are conveyed from the combustion furnace through either a copper-oxide or an iron catalytic furnace, depending upon whether the sample is tagged with Carbon-14 or tritium. The products of the catalytic furnaces are detected by means of a radioactive detector. Means are also provided for introducing gas chromatographic products into the system for detection.

18 Claims, 2 Drawing Figures

APPARATUS AND PROCESS FOR CHROMATOGRAPHIC PRODUCT DETECTION

This invention relates to chromatographic product detection. In one particular aspect, it relates to the detection of either radioactively tagged or not tagged chromatrographic products.

The prior art chromatographic detectors are basically moving wire detectors, which function by wetting the surface of the wire with a thin film of an eluant from a chromatographic column. The wire passes through an evaporator to remove the moble phase; and thence, to a combustion furnace, where the involitile solutes are converted to carbon dioxide and water. The carbon dioxide and combustion gas, e.g., oxygen are mixed with hydrogen and are passed over a nickel catalyst to convert the carbon dioxide to methane, which is then detected by a flame ionisation detector. However, the prior art detectors presently available are inadequate to fully exploit the moving wire technique of chromatographic detection. There is no provision in the prior art detectors for detecting both radioactive and non-radioactive substances within the same apparatus.

It is, therefore, an object of this invention to provide a process and apparatus for the detection of both radioactive and non-radioactive substances from chromatographic analysis.

Figure 2:
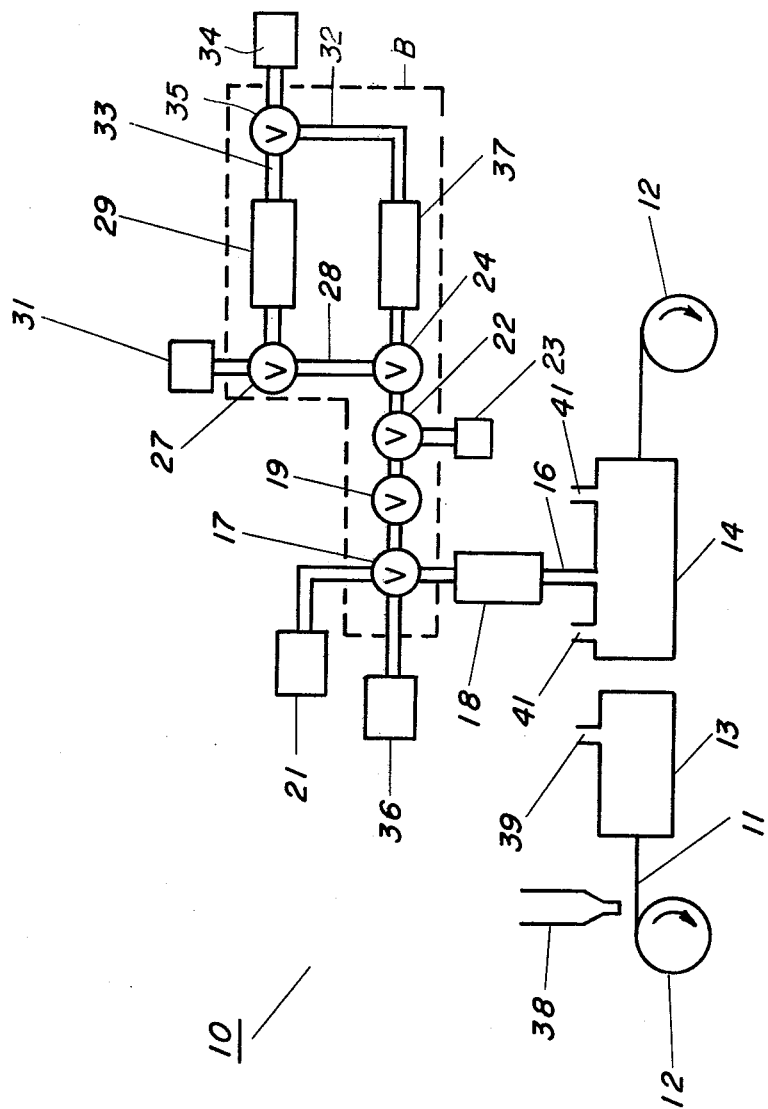

These and other objects of the invention will become apparent from the following detailed description and Drawing, wherein:

FIG. 1 schematically shows a detection apparatus of this invention;

FIG. 2 schematically shows a preferred embodiment of the apparatus of FIG. 1.

Broadly, this invention provides an apparatus for detecting products of chromatographic analysis, which products may be either radioactively tagged with Carbon-14 or tritium or not tagged; and which comprises in combination, a movable wire having sample receiving means, an evaporator oven, which is mounted in tandem with a combustion furnace. The wire is adapted to move a sample first through the evaporator oven and then through the combustion furnace. The evaporator oven is provided with gas ingress means and the combustion furnace is provided with both gas ingress means and gas egress means. The evaporator oven is adapted to remove solvent from the liquid sample leaving a solute remaining on the wire, and the combustion furnace is adapted to convert the solute into a gaseous combustion product with a combustion gas.

The combustion furnace gas egress means is in flow communication with a first valve means, which is in flow communication with the ingress means of a first catalytic furnace and a second valve means. The catalytic furnace is adapted to convert the gaseous combustion product from the combustion furnace to a gaseous reaction product. It has gas egress means, which are in flow communication with a first detector means.

This second valve means is in flow communication with a third valve means, and is adapted to emit or not the gaseous combustion product to the third valve means.

The third valve means is in flow communication with both a fourth valve means and an external, inert gas source. This valve means is adapted to either emit the gaseous combustion product to the fourth valve means or to emit an inert gas to the fourth valve means.

The fourth valve means is in flow communication with both a drying chamber and a fifth valve means. It is adapted to shunt the gaseous combustion product to either the drying chamber or to the fifth valve means.

The fifth valve means is in flow communication with a second catalytic furnace and a source of reaction gas. It is adapted to shunt the gaseous combustion product to the second catalytic furnace for conversion to a gaseous reaction product and simultaneously, emit a reaction gas to the second catalytic furnace.

The drying chamber and the second catalytic furnace are each in flow communication with a sixth valve means, which is in flow communication with a second detector means. The valve means is adapted to shunt the gaseous combustion product from the drying chamber or the gaseous reaction product from the second catalytic furnace to the second detector means.

In a preferred embodiment of this invention (FIG. 2), the combustion furnace gas egress means are in flow communication with the ingress means of the first catalytic furnace, and the gas egress means of the catalyst furnace are in flow communication with the first valve means.

This first valve means is in flow communication with both the first detector means and the second valve means.

The first valve means may also be in flow communication with a gas chromatographic sample receiving means.

The second valve means is in flow communication with the third valve means, which is in communication with the fourth valve means.

The fourth valve means is in flow communication with both a second catalytic furnace and a fifth valve means. It is adapted to shunt the gaseous reaction product from the first catalytic furnace to either a second catalytic furnace for conversion to a second gaseous reaction product or to the fifth valve means.

The fifth valve means is in flow communication with a third catalytic furnace and a source of reaction gas. It is adapted to shunt the gaseous reaction product from the first catalytic furnace to the third catalytic furnace for conversion to a third gaseous reaction product and simultaneously, emit a reaction gas to the third catalytic furnace.

The second catalytic furnace and the third catalytic furnace are each in flow communication with the sixth valve means, which valve means is in flow communication with the second detector means.

It is a further embodiment of this invention, as will be apparent to one skilled in the art that only that portion of the apparatus up-stream of the first valve means in the preferred embodiment described above need be used when it is desired to practice this invention using only samples from a gas chromatographic apparatus.

It is a feature of this invention that the first detector means is a flame ionisation detector and the second detector means is a radioactive detector.

In operation, when the chromatographic sample is a liquid; it is applied to a moving wire, which moves the sample through a evaporator oven to dry the sample, and then conveys the dried sample through a combustion furnace where the sample is combusted with a combustion gas to form carbon dioxide ($CO_2$) gas and water.

If the original chromatographic sample was non-radioactive, the carbon dioxide gas is contacted with a nickel catalytst in the first catalytic furnace to convert the gas to methane and hydrogen and conveyed directly to the flame ionisation detector.

If the chromatographic sample was radioactively tagged, then it is conveyed to either the drying chamber or the second catalytic furnace, depending upon the nature of the radioactive tagging.

If the sample was tagged with Carbon-14 (C-14), the $CO_2$ is conveyed to the drying chamber to remove the water, and then conveyed to the radioactive detector.

If the sample was tritium tagged, then the $CO_2$ gas is conveyed to the second catalytic furnace containing an iron catalyst and in the presence of hydrogen converted to tritium gas, and the gas is then conveyed to radioactive detector.

If the chromatographic sample is from a gas chromatographic (FIG. 2), then the sample is introduced downstream of the nickel catalyst furnace and conveyed through either the flame ionisation detector or the radioactive detector depending system or the radioactive detector system, depending upon whether it was radioactively tagged or not.

In operation, using the preferred embodiment of this invention (FIG. 2), the drying chamber is replaced by the second catalytic furnace (copper-oxide catalyst) and the C-14 tagged methane gas from the nickel furnace is converted to $CO_2$ gas and then shunted to the radioactive detector.

In the process of this invention, the evaporator temperature may be from 25°C to 150°C, preferably, 40°C to 80°C. The combustion temperature is from about 600°C to 1000°C, preferably, 700°C to 800°C. The preferred combustion gas is oxygen. The conversion temperature in the copper-oxide catalytic furnace is from about 600°C to 1000°C, preferably, 700°C to 800°C. The conversion temperature in the iron catalytic furnace is from about 600°C to 1000°C preferably, 700°C to 800°C.

This invention will best be understood from the following detailed description of the apparatus of this invention, wherein like numerals in the Drawing refer to like parts. Referring now to FIG. 1, there is shown generally, at 10 the chromatographic sample detector apparatus of this invention. The apparatus 10 comprises, in combination, a moving wire 11, take up spools 12, an evaporator oven 13, and a combustion furnace 14. In flow communication with the furnace 14, via conduit 16 is a valve 17. The valve 17 is in flow communication with both a nickel catalytic furnace 18 and a second valve 19, depending upon the nature of the sample introduced into the apparatus. The furnace 18 is in communication with a detector 21, which may be a flame ionisation detector.

Valve 19 is an on-off valve and either emits, or prevents gaseous flow to valve 22. Valve 22 is adapted to emit either a gas sample from valve 19 or an inert gas from an inert gas source 23 to the radioactive detection of the apparatus 10.

Valve 22 is in further flow communication with valve 24. Valve 24 is in flow communication with a drying chamber 26 or valve 27, via conduit 28. Depending upon the nature of the radioactively tagged sample, the combustion gas from furnace 14 is either shunted to the drying chamber 26 or to the iron catalytic furnace 29 by the operation of valves 24 and 27. A Carbon-14 (C-14) tagged combustion gas sample is directed to the drying chamber 26 and a tritium tagged combustion gas sample is directed to the iron catalyst furnace 29. If the gas sample is tritium tagged, valve 27 emits both the gaseous sample and hydrogen gas from a source 31 to the furnace 29. The gas sample from either the drying chamber 26 and the furnace 29 are conducted, via conduits 32 and 33 and valve 35 to the radioactive detector 34.

In a preferred embodiment of the invention shown in FIG. 2, valve 17 is shown downstream of the nickel furnace 17 and is in flow communication with detector 21, valve 19, and a gas chromatograph 36. The drying chamber 26 (see FIG. 1), is replaced by a copper-oxide (CuO) catalytic furnace 37.

In operation, a liquid sample from a chromatographic column 38 is conveyed by the moving wire 11 through the evaporator oven 13 where the solvent is evaporated and removed, via egress port 39, into the combustion furnace 14, where a combustion gas, e.g., oxygen is introduced at ingress port 41 to combust the dried solute to carbon dioxide ($CO_2$) and water. The $CO_2$ gas is then conveyed, via conduit 16 to valve 17.

If the sample from the column 38 was non-radioactive, then the $CO_2$ gas is conveyed to the nickel catalyst furnace 18 where it is converted to methane gas and hydrogen gas. The gases are then conveyed to the ionisation flame detector 21 for detection.

If the sample from column 38 was radioactively tagged with C-14, the combustion gas ($CO_2$ and water vapor) is conveyed to the drying chamber, via valves 19, 22, and 24 where water is removed and then conveyed, via conduit 32 to the radioactive detector 34.

If the sample from the column 38 was radioactively tagged with tritium, then the combustion gas is conveyed to the iron catalyst furnace 29, via valves 19, 22, and 27 where it is converted to tritium-hydrogen gas, which is conveyed, via conduit 33 to the radioactive detector 34.

When the preferred embodiment shown in FIG. 2 is used, the $CO_2$ is converted to methane in the furnace 18 and then shunted to either detector 21 or 34, depending on the radioactivity or non-radioactivity of the column sample. A C-14 tagged methane from the nickel furnace 18 sample is converted in the CuO furnace 37 to $CO_2$ and then conveyed to the radioactive detector 34.

Tritium tagged samples are conveyed to the iron furnace 29 and then to detector 34, as noted above.

Samples from a gas chromatograph 36 are conveyed to detector 21 or 34, depending on whether or not the gas sample was radioactively tagged, as stated above when only samples from a gas chromatograph are to be detected then only that portion of apparatus 10 upstream of valve 17 in FIG. 2 is necessary for sample detection.

It is desirable to maintain the gas samples at an elevated temperature in the catalyst system. For this purpose, the section of the apparatus 10 shown by the dashed lines A in FIG. 1 and B in FIG. 2 is preferably maintained at a temperature of about 450°C. This may be accomplished by means known in the art, such as heating chambers and the like.

The catalyst furances are preferably quartz catalyst tubes.

The catalysts used are known in the art. The nickel catalyst may be prepared by adsorbing a saturated solution of nickel nitrate on 20/40 BS mexh brickdust, decomposing the nitrate to the oxide by heating to 500°C for 3 hours, and reducing the oxide to metallic nickel in a stream of hydrogen at 250°C.

The iron catalyst may be steel wool.

The copper-oxide catalyst may be short rods of copper-oxide wire.

It will be understood by one skilled in the art that carbon monoxide gas (CO) may also be present with the $CO_2$ gas, and that this will not interfere with the operation of the apparatus of the invention as a chromatographic product detector, and that where the term "carbon-dioxide" is used, it is not meant to be a limitation of the invention.

What is claimed is:

1. A process for detecting products of liquid chromatographic analysis, which products may be either radioactively tagged with Carbon-14 or tritium or not tagged which comprises the steps of:
   a. Applying either a radioactively Carbon-14 tagged, a tritium tagged or a non-tagged chromatographic sample to a moving wire;
   b. Moving the sample on the wire first through an evporator oven to dry the sample, and then through a combustion furnace to combust the sample with a combustion gas to form either non-radioactive or Carbon-14 tagged or tritium tagged carbon dioxide gas and water;
   c. When non-radioactive carbon dioxide gas is formed in step b), contacting the non-radioactive carbon dioxide gas with a nickel catalyst in a first catalytic furnace to convert the carbon dioxide gas to non-radioactive methane and hydrogen;
   d. Conveying non-radioactive methane to a first detector means for sample detection;
   e. When Carbon-14 tagged radioactive carbon dioxide gas is formed in step b), conveying the Carbon-14 tagged radioactive carbon dioxide and water to a drying chamber to remove the water, and conveying the carbon dioxide gas to a second detector means for sample detection;
   f. When tritium tagged radioactive carbon dioxide gas is formed in step b), conveying the tritium tagged radioactive water and carbon dioxide gas to a second catalytic furnace and contacting the water with an iron catalyst in the presence of hydrogen to convert the water to tritium gas and conveying the tritium gas to the second detector means for sample detection.

2. The process according to claim 1, wherein the conversion temperature in the first catalytic furnace is from 600°C to 1000°C.

3. The process according to claim 2, wherein the conversion temperature in the second catalytic furnace is from 600°C to 1000°C.

4. The process according to claim 3, wherein the combustion gas is oxygen.

5. A process for detecting products of liquid chromatographic analysis, which products may be either radioactively tagged with Carbon-14 or tritium or not tagged, which comprises the steps of:
   a. Applying either a radioactively Carbon-14 tagged, a tritium tagged or a non-tagged chromatographic sample to a moving wire;
   b. Moving the sample on the wire first through an evaporator oven to dry the sample, and then through a combustion furnace to combust the sample with a combustion gas to form either non-radioactive or Carbon-14 tagged or tritium tagged carbon dioxide gas and water;
   c. When non-radioactive carbon dioxide gas is formed in step b), contacting the carbon dioxide gas with a nickel catalyst in a first catalytic furnace to convert the carbon dioxide gas to methane and hydrogen;
   d. Conveying non-radioactive methane to a first detector means for sample detection;
   e. When Carbon-14 tagged radioactive carbon dioxide gas is formed in step b), conveying Carbon-14 tagged methane to a second catalytic furnace and contacting the methane with a copper-oxide catalyst to convert the methane to carbon dioxide gas and conveying the carbon dioxide gas to a second detector means for sample detection;
   f. When tritium tagged radioactive methane is formed in step b), conveying tritium tagged methane to a third catalytic furnace and contacting the methane with an iron catalyst in the presence of hydrogen to convert the methane to tritium gas and conveying the tritium gas to the second detector means for sample detection.

6. The process according to claim 5, wherein the conversion temperature in the first catalytic furnace is from 600°C to 1000°C.

7. The process according to claim 6, wherein the conversion temperature in the second catalytic furnace is from 600°C to 1000°C.

8. The process according to claim 7, wherein the conversion temperature in the third catalytic furnace is from 600°C to 1000°C.

9. The process according to claim 8, wherein the combustion gas is oxygen.

10. A process for detecting products of a gas chromatographic analysis, which products may be either radioactively tagged with Carbon-14 or tritium, or not tagged which comprises the steps of:
    a. Conveying a non-tagged gas chromatographic sample from the gas chromatograph to a first detector means for sample detection;
    b. Conveying a Carbon-14 tagged gas chromatographic sample from the gas chromatograph to a first catalytic furnace and contacting the gas sample with copper-oxide to convert the gas sample to carbon dioxide gas and conveying the carbon dioxide gas to a second detector means for sample detection;
    c. Conveying a tritium tagged gas chromatographic sample from the gas chromatograph to a second catalytic furnace and contacting the gas sample with an iron catalyst in the presence of hydrogen to convert the gas sample to tritium gas, and conveying the tritium gas to the second detector means for sample detection.

11. The process according to claim 10, wherein the conversion temperature in both the first catalytic furnace and the second catalytic furnace is from 600° to 1000°C.

12. An apparatus for detecting products of chromatographic analysis, which products may be either radioactively tagged or not tagged which comprise in combination:
    a. A movable wire having liquid chromatographic sample receiving means;
    b. An evaporator oven mounted in tandem with a combustion furnace, the wire adapted to move a sample first through the evaporator oven and then through the combustion furnace;
    c. The evaporator oven having gas egress means, and the combustion furance having at least one gas ingress means and gas egress means; the evaporator oven adapted to remove solvent from a liquid sample leaving a solute remaining on the wire, and the combustion furnace adapted to convert the solute to a gaseous combustion product with a combustion gas;

d. The combustion furnace gas egress means in flow communication with a first valve means;

e. The first valve means in flow communication with ingress means for a first catalytic furnace; and a second valve means; the catalytic furnace, adapted to convert the gaseous combustion product from the combustion furnace to a gaseous reaction product and having gas egress means in flow communication with a first detector means;

f. The second valve means in flow communication with a third valve means and adapted to emit or not the gaseous combustion product to the third valve means;

g. The third valve means in flow communication with a fourth valve means and an external, inert gas source, and adapted to either emit the gaseous combustion product to the fourth valve means or to emit the inert gas to the fourth valve means;

h. The fourth valve means in flow communication with a drying chamber and a fifth valve means, and adapted to shunt the gaseous combustion product to either the drying chamber or to the fifth valve means;

i. The fifth valve means in flow communication with a second catalytic furnace and a source of reaction gas, and adapted to shunt the gaseous combustion product to the second catalytic furnace for conversion to a gaseous reaction product, and simultaneously, emit a reaction gas to the second catalytic furnace;

j. The drying chamber and the second catalytic furnace each in flow communication with a sixth valve means, which valve means is in flow communication with a second detector means, the valve means adapted to shunt the gaseous combustion product from the drying chamber or the gaseous reaction product from the second catalytic furnace to the second detector means.

13. The apparatus according to claim 12, wherein the first detector means is a flame ionisation detector, and the second detector means is a radioactive detector.

14. An apparatus for detecting products of chromatographic analysis, which products may be either radioactively tagged or not tagged, which comprise in combination:

a. A movable wire having liquid chromatographic sample receiving means;

b. An evaporator oven mounted in tandem with a combustion furnace, the wire adapted to move a sample first through the evaporator oven, and then through the combustion furnace;

c. The evaporator oven having gas egress means, and the combustion furnace having at least one gas ingress means and gas egress means, the evaporator oven adapted to remove solvent from a liquid sample leaving a solute remaining on the wire, and the combustion furnace adapted to convert the solute to a gaseous combustion product with a combustion gas;

d. The combustion furnace gas egress means in flow communication with ingress means for a first catalytic furnace; the catalytic furance, adapted to convert the gaseous combustion product from the combustion furnace to a gaseous reaction product and having gas egress means in flow communication with a first valve means;

e. The first valve means in flow communication with a first detector means and a second valve means and adapted to shunt the gaseous reaction product to the first detector means or the second valve means;

f. The second valve means in flow communication with a third valve means and adapted to emit or not the gaseous reaction product to the third valve means;

g. The third valve means in flow communication with a fourth valve means and an external, inert gas source and adapted to either emit the gaseous reaction product to the fourth valve means or to emit the inert gas to the fourth valve means;

h. The fourth valve means in flow communication with a second catalytic furnace and a fifth valve means, and adapted to shunt the gaseous reaction product to either the second catalytic furnace for conversion to a second gaseous reaction product or to the fifth valve means;

i. The fifth valve means in flow communication with a third catalytic furnace and a source of reaction gas, and adapted to shunt the gaseous reaction product to the third catalytic furnace for conversion to a third gaseous reaction product, and simultaneously, emit a reaction gas to the third catalytic furnace;

j. The second catalytic furnace and the third catalytic furnace each in flow communication with a sixth valve means, which valve means is in flow communication with a second detector means, the valve means adapted to shunt the gaseous reaction product from the second catalytic furnace or the third catalytic furnace to the second detector means.

15. The apparatus according to claim 14, wherein the first valve means is also in flow communication with gas chromatographic sample receiving means.

16. The appratus according to claim 15, wherein the first detector means in a flame ionisation detector, and the second detector means is a radioactive detector.

17. An apparatus for detecting products of chromatographic analysis, which products may be either radioactively tagged or not tagged, which comprise in combination:

a. A first valve means in flow communication with a gas chromatographic sample receiving means, a first detector means, and a second valve means and adapted to shunt the gas chromatographic sample to the first detector means or the second valve means;

b. The second valve means in flow communication with a third valve means and adapted to emit or not the gas chromatographic sample to the third valve means;

c. The third valve means in flow communication with a fourth valve means and an external, inert gas source and adapted to either emit the gas chromatographic sample to the fourth valve means or to emit the inert gas to the fourth valve means;

d. The fourth valve means in flow communication with a first catalytic furnace and a fifth valve means, and adapted to shunt the gas chromatographic sample to either the first catalytic furnace for conversion to a gaseous reaction product or to the fifth valve means;

e. The fifth valve means in flow communication with a second catalytic furnace and a source of reaction gas, and adapted to shunt the chromatographic sample to the second catalytic furnace for conversion to a gaseous reaction product and simultaneously, emit a reaction gas to the third catalytic furnace;

f. The first catalytic furnace and the second catalytic furnace each in flow communication with a sixth valve means, which valve means is in flow communication with a second detector means, the valve means adapted to shunt the gaseous reaction product from the second catalytic means.

18. The apparatus according to claim 17, wherein the first detector means is a flame ionisation detector, and the second detector means is a radioactive detector.

* * * * *